(12) United States Patent
Kudo

(10) Patent No.: US 9,784,964 B2
(45) Date of Patent: Oct. 10, 2017

(54) IMAGE PICKUP UNIT FOR ENDOSCOPE HAVING MULTIPLE BONDED FRAMES

(71) Applicant: OLYMPUS CORPORATION, Tokyo (JP)

(72) Inventor: Akira Kudo, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/366,005

(22) Filed: Dec. 1, 2016

(65) Prior Publication Data

US 2017/0082848 A1   Mar. 23, 2017

Related U.S. Application Data

(63) Continuation of application No. PCT/JP2015/076004, filed on Sep. 14, 2015.

(30) Foreign Application Priority Data

Nov. 19, 2014   (JP) ................................. 2014-234881

(51) Int. Cl.
*A61B 1/05*       (2006.01)
*A61B 1/055*      (2006.01)
(Continued)

(52) U.S. Cl.
CPC ............ *G02B 23/2484* (2013.01); *A61B 1/00* (2013.01); *A61B 1/00163* (2013.01); *A61B 1/04* (2013.01);
(Continued)

(58) Field of Classification Search
CPC .............. A61B 1/00177; A61B 1/0011; A61B 1/00163; A61B 1/05; A61B 1/00096;
(Continued)

(56) References Cited

U.S. PATENT DOCUMENTS 6,547,722 B1 * 4/2003 Higuma ............. A61B 1/00096
                                                         600/133
6,767,322 B1 * 7/2004 Futatsugi ........... A61B 1/00096
                                                         600/129
(Continued)

FOREIGN PATENT DOCUMENTS

EP       1769719 A1      4/2007
JP      H04-10809 A      2/1992
(Continued)

OTHER PUBLICATIONS

International Search Report dated Dec. 15, 2015 issued in PCT/JP2015/076004.
English Abstract only of JP H01-104235 A1, dated Apr. 21, 1989.

*Primary Examiner* — John P Leubecker
(74) *Attorney, Agent, or Firm* — Scully, Scott, Murphy & Presser, P.C.

(57) ABSTRACT

An image pickup unit for endoscope is configured such that a first lens frame and a second lens frame are fitted to each other with a first fitting area and bonded and fixed to each other with a first adhesive at a first frame fixing portion, the second lens frame and a holding frame are fitted to each other with a second fitting area and bonded and fixed to each other with a second adhesive at a second frame fixing portion, the first lens frame, the second lens frame, and the fixing frame are bonded and fixed together with the second adhesive, the second fitting area is larger than the first fitting area, and the second adhesive has a glass transition temperature lower than a glass transition temperature of the first adhesive.

4 Claims, 11 Drawing Sheets

(51) Int. Cl.
  *G02B 23/24*   (2006.01)
  *A61B 1/04*   (2006.01)
  *G02B 23/26*   (2006.01)
  *G02B 7/02*   (2006.01)
  *H04N 5/225*   (2006.01)
  *A61B 1/00*   (2006.01)

(52) U.S. Cl.
  CPC ........... G02B 7/025 (2013.01); G02B 23/243 (2013.01); G02B 23/26 (2013.01); H04N 5/2254 (2013.01); *A61B 1/00096* (2013.01); *A61B 1/00177* (2013.01); *H04N 2005/2255* (2013.01)

(58) Field of Classification Search
  CPC ........... G02B 23/2484; G02B 23/2423; G02B 23/243; G02B 7/025; H04N 5/2254; H04N 2005/2255
  See application file for complete search history.

(56) References Cited

U.S. PATENT DOCUMENTS

| | | |
|---|---|---|
| 2007/0118019 A1 | 5/2007 | Mitani et al. |
| 2009/0043166 A1* | 2/2009 | Ishii ..................... A61B 1/0011 600/130 |
| 2009/0062615 A1* | 3/2009 | Yamaya ............. A61B 1/00177 600/167 |
| 2009/0067067 A1* | 3/2009 | Yamaya ............. A61B 1/00177 359/813 |
| 2010/0073470 A1* | 3/2010 | Takasaki ................ A61B 1/051 348/76 |
| 2012/0323076 A1* | 12/2012 | Ishii ................... A61B 1/00004 600/133 |
| 2013/0120647 A1* | 5/2013 | Negishi .................. G02B 7/022 348/374 |
| 2014/0043454 A1* | 2/2014 | Kato .................. A61B 1/00163 348/68 |

FOREIGN PATENT DOCUMENTS

| | | |
|---|---|---|
| JP | 2004-216174 A | 8/2004 |
| JP | 2006-015076 A | 1/2006 |
| JP | 2008-200159 A | 9/2008 |
| JP | 2009-273642 A | 11/2009 |
| JP | 2013-059438 A | 4/2013 |
| WO | 2006/004123 A1 | 1/2006 |

* cited by examiner

IMAGE PICKUP UNIT FOR ENDOSCOPE HAVING MULTIPLE BONDED FRAMES

CROSS REFERENCE TO RELATED APPLICATION

This application is a continuation application of PCT/JP2015/076004 filed on Sep. 14, 2015 and claims benefit of Japanese Application No. 2014-234881 filed in Japan on Nov. 19, 2014, the entire contents of which are incorporated herein by this reference.

BACKGROUND OF THE INVENTION

1. Field of the Invention

The present invention relates to an image pickup unit for endoscope including a solid-state image pickup device built in an insertion portion of an endoscope.

2. Description of the Related Art

In recent years, an endoscope has been used in a medical field and an industrial field. The endoscope can perform observation, treatment, and the like by inserting an elongated insertion portion into a tube with a small diameter. Reduction in the diameter of the insertion portion and shortening of a rigid portion are demanded in the endoscope in order to improve an insertion property.

In a so-called electronic endoscope including an image pickup unit for endoscope (hereinafter, abbreviated as an image pickup unit) built in a distal end portion of an insertion portion, the number of pixels of a solid-state image pickup device is increased, for example, in order to improve an observation performance.

In the image pickup unit, an objective lens unit and an image pickup device unit including the solid-state image pickup device are integrated. The image pickup device unit is an expensive unit among the units included in the endoscope.

The objective lens unit includes optical lenses that are a plurality of optical members, an interval ring, a diaphragm, and the like, which are fixed and installed in a lens frame.

On the other hand, the image pickup device unit mainly includes: a solid-state image pickup device (hereinafter, abbreviated as an image pickup device), such as a CCD and a C-MOS; a circuit substrate on which the image pickup device and various electronic components are mounted; and a plurality of signal lines connected to the circuit substrate.

The objective lens unit and the image pickup device unit are formed as an image pickup unit in which a lens frame forming the objective lens unit and a holding frame forming the image pickup device unit are integrated and fixed by bonding or joining.

Japanese Patent Application Laid-Open Publication No. 2009-273642 illustrates an image pickup unit for endoscope in which positioning of optical performance is facilitated to improve assembly work efficiency, and a waterproof and moisture barrier property is improved. In the image pickup unit for endoscope, a prism unit is provided with a first lens holding frame attachment portion and a second lens holding frame attachment portion in which optical axes are aligned. Therefore, the first lens holding frame attachment portion is installed on a first lens unit, and the second lens holding frame attachment portion is installed on a second lens unit. As a result, the optical axes can be easily aligned, and the assembly work efficiency becomes excellent. Note that a holder tube of an image pickup device holder is fitted and fixed onto the second lens unit.

Japanese Patent Application Laid-Open Publication No. 2006-015076 illustrates an image pickup apparatus that allows reusing a component before exchange when an image pickup unit is repaired and exchanged. In the image pickup apparatus, a fixing member is used for fixation of a lens frame and a CCD holding frame. When the lens frame and the CCD holding frame are coupled, an adhesive or the like is not used for an attachment surface (fitting portion) coming into contact with both of a proximal end side outer circumference surface of the lens frame and a distal end side inner circumference surface of the CCD holding frame.

Note that it is assumed that a first frame member and a second frame member are respectively provided on a distal end side and a proximal end side across one frame member, and frame members are integrated and fixed by providing frame fixing portions based on joining or bonding. In this case, if a fitting area of a first frame fixing portion provided on the distal end side of the frame member and a fitting area of a second frame fixing portion provided on the proximal end side of the frame member are different, and a same adhesive is applied to respective fitting surfaces to provide the first frame fixing portion and the second frame fixing portion, the frame fixing portion with a small fitting area is broken up by a smaller load than the frame fixing portion with a large fitting area when a load is applied to break up the frame fixing portions.

SUMMARY OF THE INVENTION

An aspect of the present invention provides an image pickup unit for endoscope including: an objective lens unit including a first lens frame and a second lens frame; an image pickup device unit including an image pickup device and a holding frame configured to hold the image pickup device; a first frame fixing portion at which the first lens frame and the second lens frame are fitted to each other; and a second frame fixing portion at which the second lens frame and the holding frame are fitted to each other, wherein the first lens frame and the second lens frame are fitted to each other with a first fitting area and bonded and fixed to each other with a first adhesive at the first frame fixing portion, the second lens frame and the holding frame are fitted to each other with a second fitting area and bonded and fixed to each other with a second adhesive at the second frame fixing portion, the first lens frame, the second lens frame, and the holding frame are bonded and fixed together with the second adhesive, the second fitting area is larger than the first fitting area, and the second adhesive has a glass transition temperature lower than a glass transition temperature of the first adhesive.

Another aspect of the present invention provides an image pickup unit for endoscope including: an objective lens unit including a first lens frame and a second lens frame; an image pickup device unit including an image pickup device and a holding frame configured to hold the image pickup device; a first frame fixing portion at which the first lens frame and the second lens frame are fitted to each other; and a second frame fixing portion at which the second lens frame and the holding frame are fitted to each other, wherein the first lens frame and the second lens frame are fitted to each other with a first fitting area and joined to each other by metal junction with a metal junction member at the first frame fixing portion, the second lens frame and the holding frame are fitted to each other with a second fitting area and bonded and fixed to each other with an adhesive at the second frame fixing portion, the first lens frame, the second lens frame, and the holding frame are bonded and fixed

DETAILED DESCRIPTION OF THE PREFERRED EMBODIMENT(S)

Figure 1:
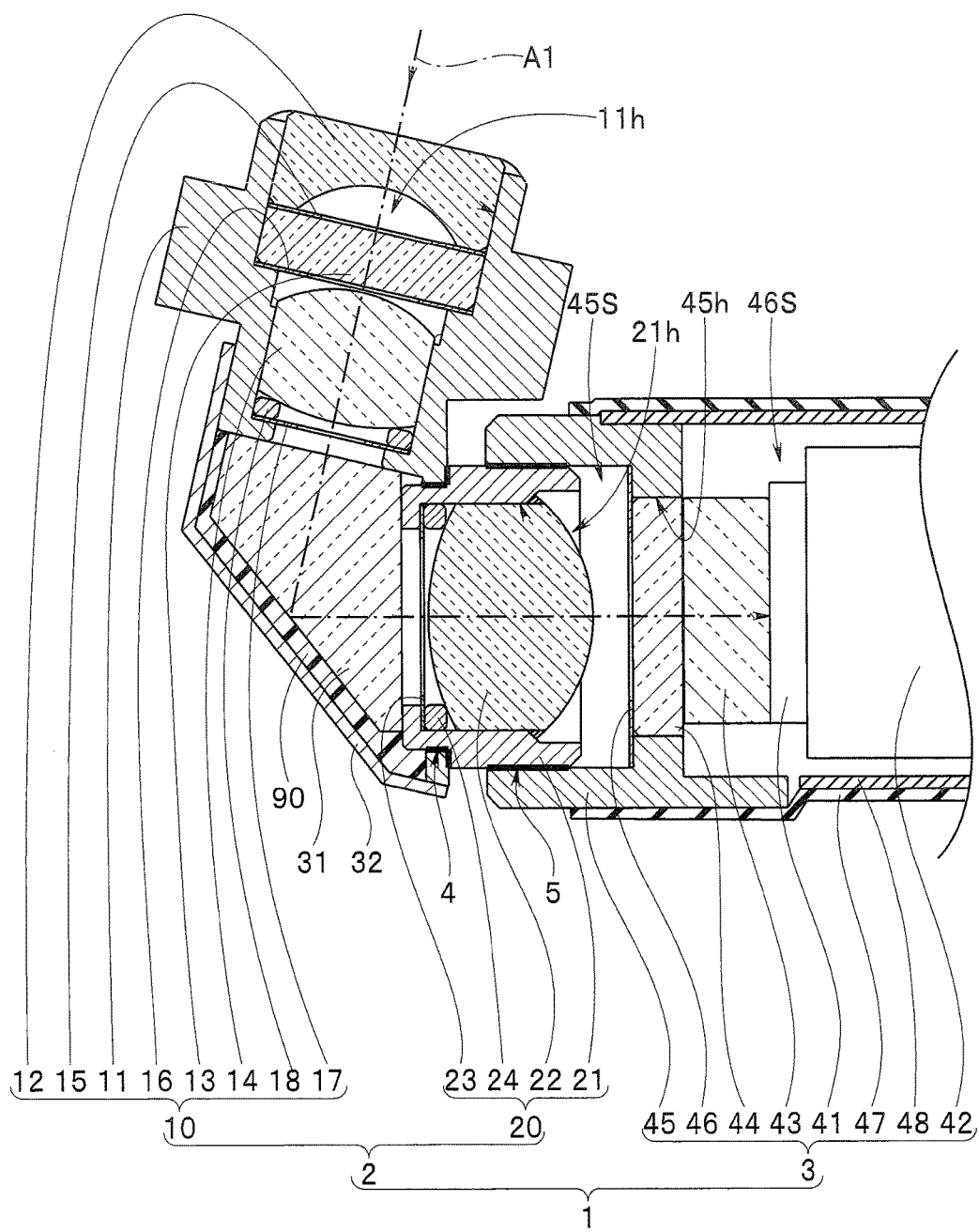
FIG. 1 is a diagram describing an example of configuration of an image pickup unit for endoscope.

Hereinafter, an embodiment of the present invention will be described with reference to the drawings.

Note that scaling of each constituent element may vary in each drawing used in the following description in order to illustrate each constituent element in a size that allows recognizing the constituent element on the drawing. That is, the present invention is not limited only to quantities of the constituent elements, shapes of the constituent elements, ratios of the sizes of the constituent elements, and relative positional relationships between respective constituent elements described in the drawings.

An image pickup unit for endoscope shown in FIG. 1 is an image pickup unit 1 for a side-view type endoscope.

The image pickup unit 1 includes an objective lens unit 2 and an image pickup device unit 3. The objective lens unit 2 includes a first lens unit 10, a second lens unit 20, and a prism 31.

Reference sign 4 denotes a first frame fixing portion described later configured to bond and fix lens units included in the objective lens unit 2. Reference sign 5 denotes a second frame fixing portion described later configured to bond and fix the objective lens unit and the image pickup device unit.

The first lens unit 10 includes: a first lens frame 11; a plurality of optical lenses 12, 13, and 14 that are a plurality of optical members; a plurality of diaphragms 15, 16, and 17; and an interval ring 18.

Figure 2:
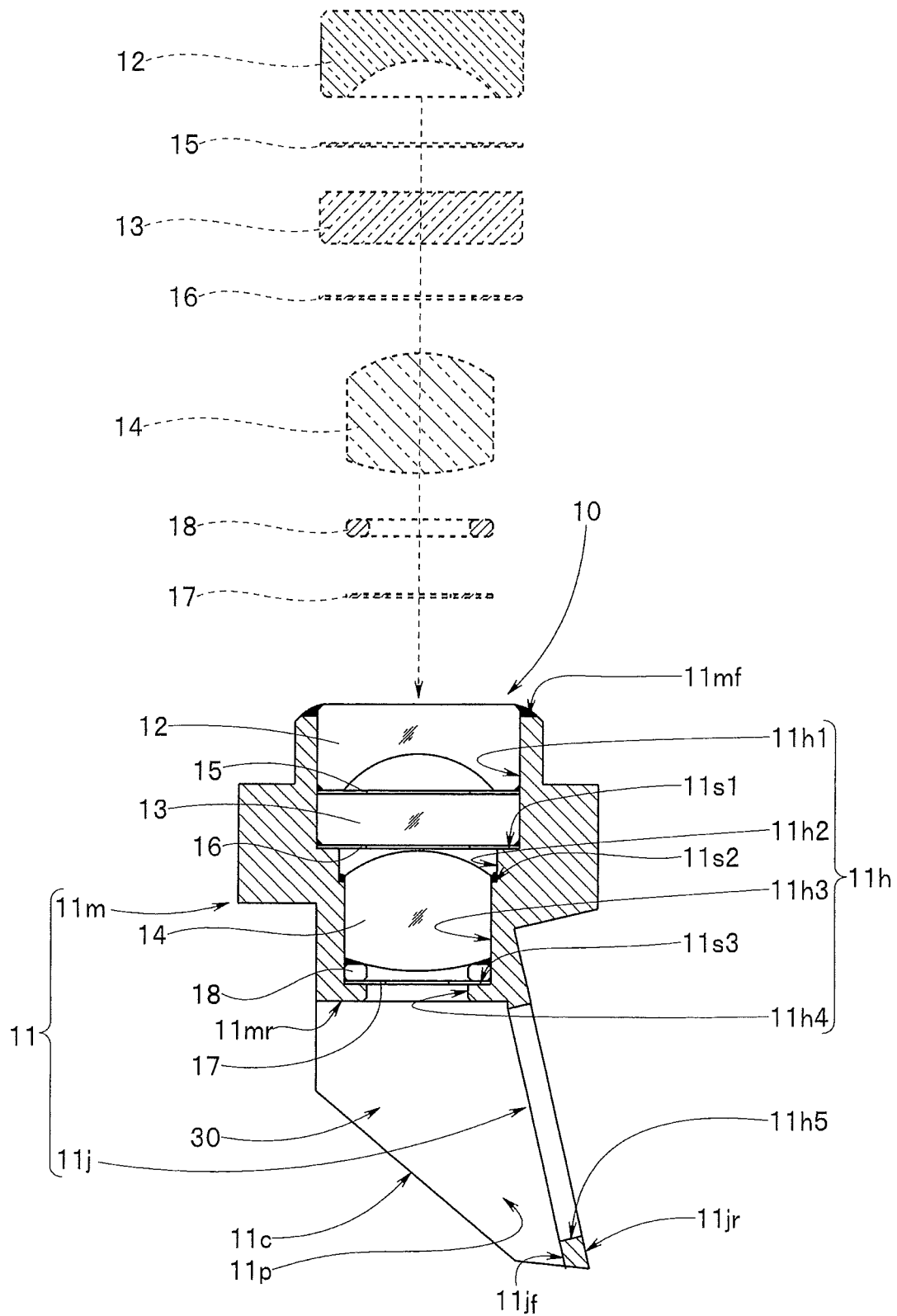
FIG. 2 is a diagram describing a first lens unit included in an objective lens unit.

As shown in FIG. 2, the first lens frame 11 includes a frame main body 11$m$ and a coupling portion 11$j$. The coupling portion 11$j$ is a convex portion protruding in a predetermined direction by a predetermined distance from a main body proximal end surface 11$mr$ of the frame main body 11$m$. Reference sign 11$p$ denotes prism storage side surfaces forming a prism housing portion 30 described later, and reference sign 11$c$ denotes cover contact surfaces described later.

A lens frame fixing hole 11$h$5 that is a through hole and that leads to the prism housing portion 30 is provided on the coupling portion 11$j$. A small diameter portion 21$a$ of a second lens frame 21 described later is fitted to the lens frame fixing hole 11$h$5. Reference sign 11$jr$ denotes a coupling portion proximal end surface, and reference sign 11$jf$ denotes a coupling portion distal end surface.

The frame main body 11$m$ has a predetermined pipe shape and includes a first frame hole 11$h$. The first frame hole 11$h$ is a stepped through hole. In order from a main body distal end surface 11$mf$ side, a first hole 11$h$1, a second hole 11$h$2, a third hole 11$h$3, and a fourth hole 11$h$4 are formed, and a first step surface 11$s$1, a second step surface 11$s$2, and a third step surface 11$s$3 are provided.

Note that the main body distal end surface 11$mf$ is a plane surface orthogonal to a center axis of the first frame hole 11$h$, and the first step surface 11$s$1, the second step surface 11$s$2, and the third step surface 11$s$3 are also plane surfaces parallel to the main body distal end surface 11$mf$. Hole diameters of the respective holes are set to predetermined sizes. The first hole 11$h$1 has a largest diameter, and the diameters decrease in order of the second hole 11$h$2, the third hole 11$h$3, and the fourth hole 11$h$4. An opening of the first frame hole 11$h$ leading to the prism housing portion 30 is an opening of the fourth hole 11$h$4.

In the present embodiment, the third diaphragm 17 and the interval ring 18 are sequentially housed in the third hole 11$h$3, and the third diaphragm 17 is arranged on the third step surface 11$s$3. The interval ring 18 is brought into contact with and arranged on the third diaphragm 17, and the interval ring 18 is bonded and fixed by an adhesive.

The third optical lens 14 is housed in the third hole 11$h$3. The third optical lens 14 is brought into contact with and arranged on the interval ring 18 and bonded and fixed. A distal end portion of the third optical lens 14 protrudes by a predetermined distance from the second step surface 11$s$2 in the state that the lens 14 is brought into contact with and arranged on the interval ring 18. The adhesive is applied to an adhesive reservoir formed by distal end portion outer circumference surfaces of the second step surface 11$s$2 and the third optical lens 14.

Note that the interval ring 18 may be brought into contact with and arranged on the third diaphragm 17 without bonding and fixing the interval ring 18. In this case, the third optical lens 14 is brought into contact with and arranged on the interval ring 18 brought into contact with and arranged on the third diaphragm 17. The third optical lens 14 is bonded and fixed, and the interval ring 18 is arranged in the third hole 11h3.

The second diaphragm 16, the second optical lens 13, the first diaphragm 15, and the first optical lens 12 are sequentially housed in the first hole 11h1, and the second diaphragm 16 is arranged on the first step surface 11s1. Each of the second optical lens 13, the first diaphragm 15, and the first optical lens 12 is brought into contact with and arranged on the second diaphragm 16 and bonded and fixed.

The adhesive is applied to a distal end portion outer circumference surface of the first optical lens 12 protruding by a predetermined distance from the main body distal end surface 11mf and applied to the main body distal end surface 11mf.

Note that the configuration of the first lens unit is not limited to the configuration described above. The numbers, the sizes, the shapes, and the like of the optical lenses, the diaphragms, and the interval rings are appropriately set, and a first lens frame corresponding to these is formed. When the first optical lens 12 is fixed by brazing, predetermined plating is applied in advance to the first optical lens 12.

As shown in FIG. 1, the second lens unit 20 includes the second lens frame 21, optical lenses 22 that are a plurality of optical members, a diaphragm 23, and an interval ring 24.

Figure 3:
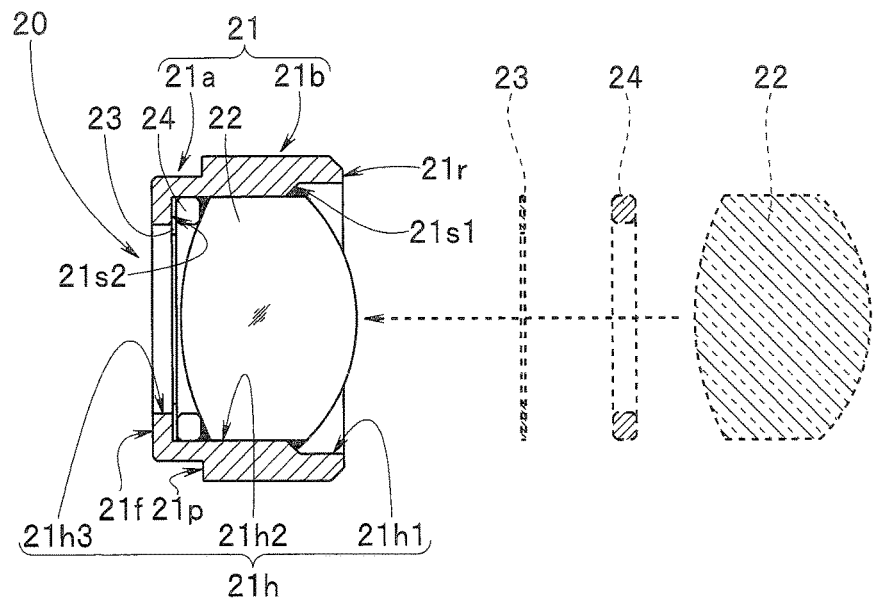
FIG. 3 is a diagram describing a second lens unit included in the objective lens unit.

As shown in FIG. 3, the second lens frame 21 is a stepped pipe including the small diameter portion 21a and a large diameter portion 21b. The small diameter portion 21a is a fitting portion for the coupling portion 11j of the first lens frame 11, and the large diameter portion 21b is a fitting portion for an image pickup device holding frame 45 described later.

The second lens frame 21 includes a second frame hole 21h. The second frame hole 21h is a stepped through hole. In order from a second lens frame proximal end surface 21r side, a first hole 21h1, a second hole 21h2, and a third hole 21h3 are formed, and a first step surface 21s1 and a second step surface 21s2 are provided.

Note that the second lens frame proximal end surface 21r is a plane surface orthogonal to a center axis of the second frame hole 21h. The first step surface 21s1 is an inclined surface, and a second step surface 21s2 is a plane surface parallel to the second lens frame proximal end surface 21r. Hole diameters of the respective holes are set to predetermined sizes. The first hole 21h1 has a largest diameter, and the diameters decrease in order of the second hole 21h2 and the third hole 21h3.

In the present embodiment, the diaphragm 23 and the interval ring 24 are sequentially housed in the second hole 21h2, and the diaphragm 23 is arranged on the second step surface 21s2. The interval ring 24 is brought into contact with and arranged on the second step surface 21s2 and bonded and fixed by an adhesive.

The optical lenses 22 are housed in the second hole 21h2. The optical lenses 22 are brought into contact with and arranged on the interval ring 24 and bonded and fixed. A proximal end portion of the optical lenses 22 protrudes by a predetermined distance from a proximal end side of the second hole 21h2 in the state that the lenses 22 are brought into contact with and arranged on the interval ring 24. The adhesive is applied to an adhesive reservoir formed by distal end portion outer circumference surfaces of the first step surface 21s1 and the optical lenses 22.

Note that the interval ring 24 may be brought into contact with and arranged on the diaphragm 23 without bonding and fixing the interval ring 24. In this case, the optical lenses 22 are brought into contact with and arranged on the interval ring 24 brought into contact with and arranged on the diaphragm 23. The optical lenses 22 are bonded and fixed, and the interval ring 24 is arranged in the second hole 21h2.

Reference sign 21f denotes a second lens frame distal end surface, and reference sign 21p denotes a positioning surface. The positioning surface 21p is a contact surface coming into contact with the proximal end surface 11jr of the coupling portion 11j. Although the first step surface 21s1 is an inclined surface in the present embodiment, the first step surface 21s1 may be a plane surface parallel to the second lens frame proximal end surface 21r. The configuration of the second lens unit is not limited to the configuration described above. The numbers, the sizes, the shapes, and the like of the optical lenses, the diaphragms, and the interval rings are appropriately set, and a second lens frame corresponding to these is formed.

Assembly of the first lens unit 10 and the second lens unit 20 will be described with reference to FIG. 4.

Figure 4:
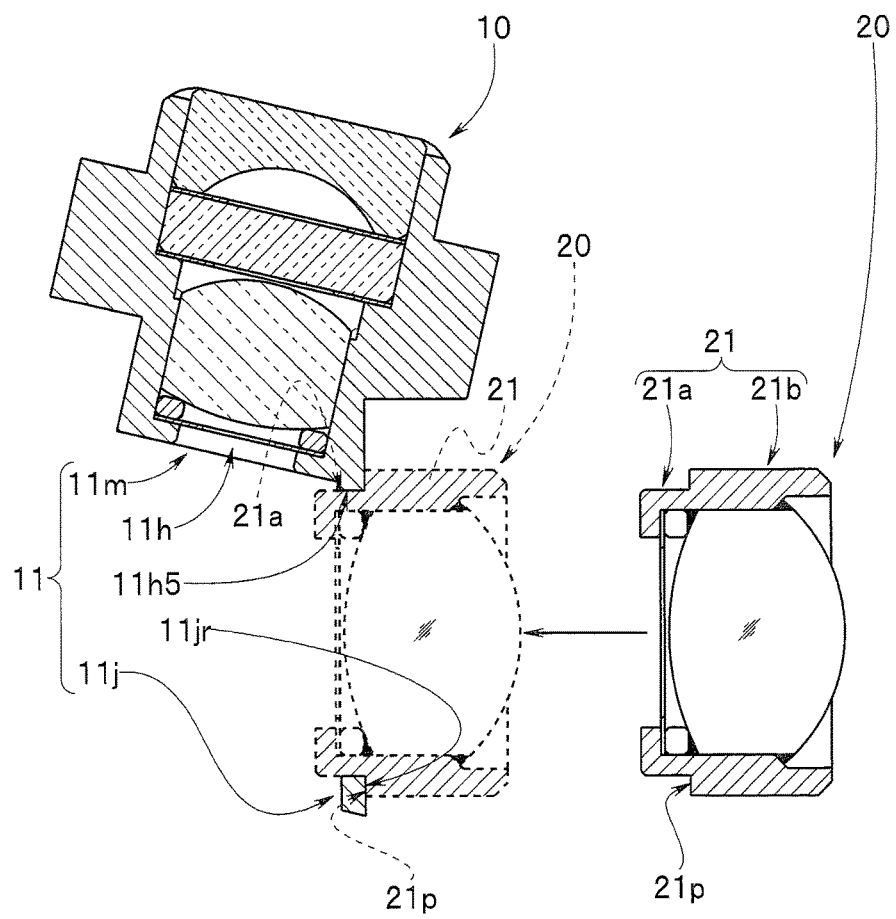
FIG. 4 is a diagram describing assembly of the first lens unit and the second lens unit.

To integrate and assemble the first lens unit 10 and the second lens unit 20 shown in FIG. 4, the coupling portion 11j provided on the first lens frame 11 included in the first lens unit 10 and the small diameter portion 21a provided on the second lens frame 21 included in the second lens unit 20 are bonded and fixed.

More specifically, the small diameter portion 21a of the second lens frame 21 is fitted and arranged in the lens frame fixing hole 11h5 of the coupling portion 11j. In this case, the positioning surface 21p of the second lens frame 21 is brought into contact with and arranged on the coupling portion proximal end surface 11jr of the coupling portion 11j. In this contact state, the first adhesive is cured to fix the small diameter portion 21a of the second lens frame 21 in the lens frame fixing hole 11h5 of the coupling portion 11j.

As a result, the coupling portion 11j provided on the first lens frame 11 and the small diameter portion 21a of the second lens frame 21 indicated by dashed lines are integrated and fixed by the first frame fixing portion 4 formed by curing of the first adhesive. The first lens unit 10 and the second lens unit 20 are assembled in a predetermined state.

Note that the first adhesive is applied in advance to an outer circumference surface of the small diameter portion 21a that is a first fitting surface of the second lens frame 21 before the small diameter portion 21a is fitted and arranged in the lens frame fixing hole 11h5 that is a first fitting surface of the coupling portion 11j, or the first adhesive is supplied to a gap between the outer circumference surface of the small diameter portion 21a and an inner circumference surface of the lens frame fixing hole 11h5 after the small diameter portion 21a of the second lens frame 21 is fitted and arranged in the lens frame fixing hole 11h5.

Figure 5A:
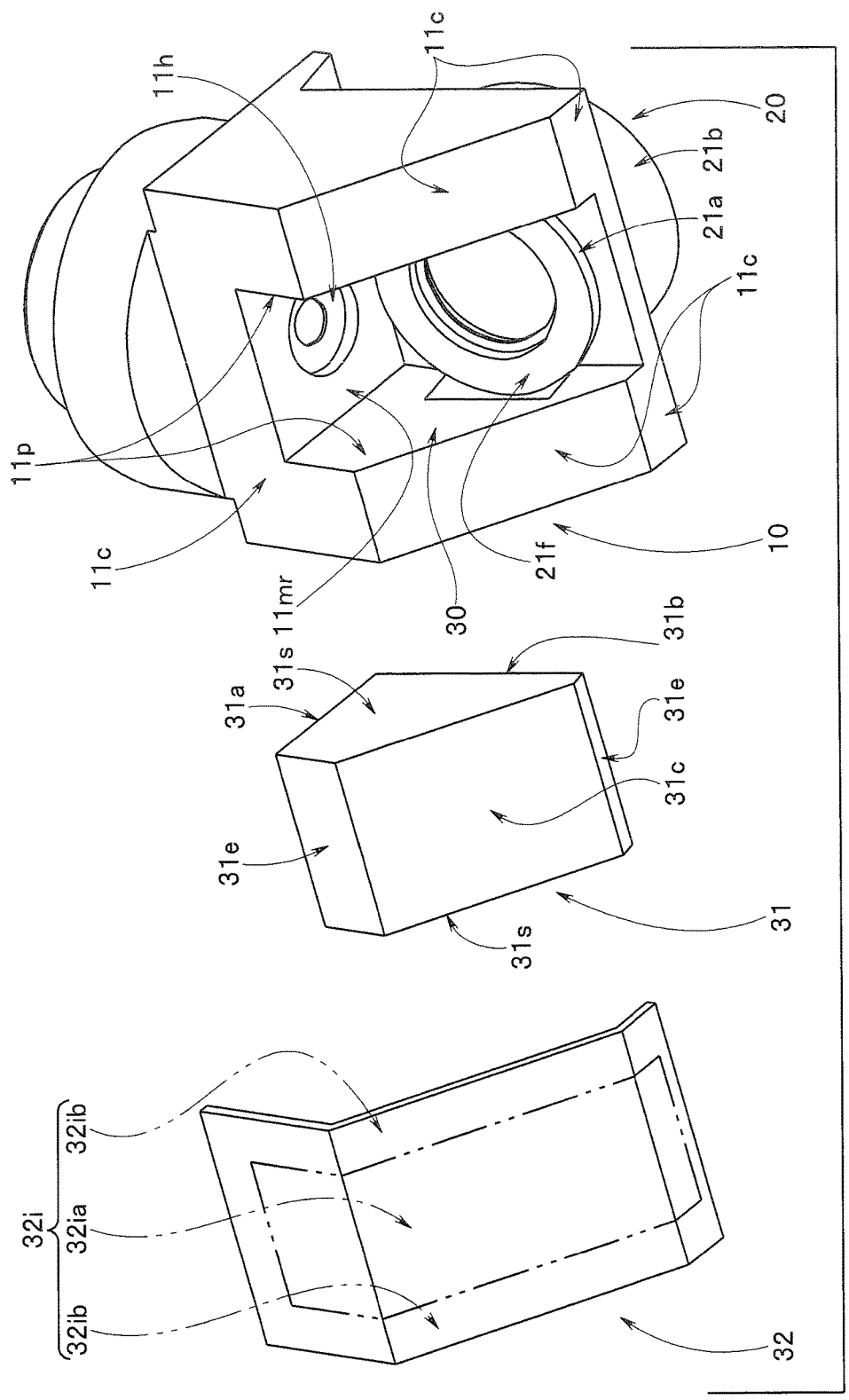
FIG. 5A is a diagram describing a relationship between a first lens frame and a prism.
Figure 5B:
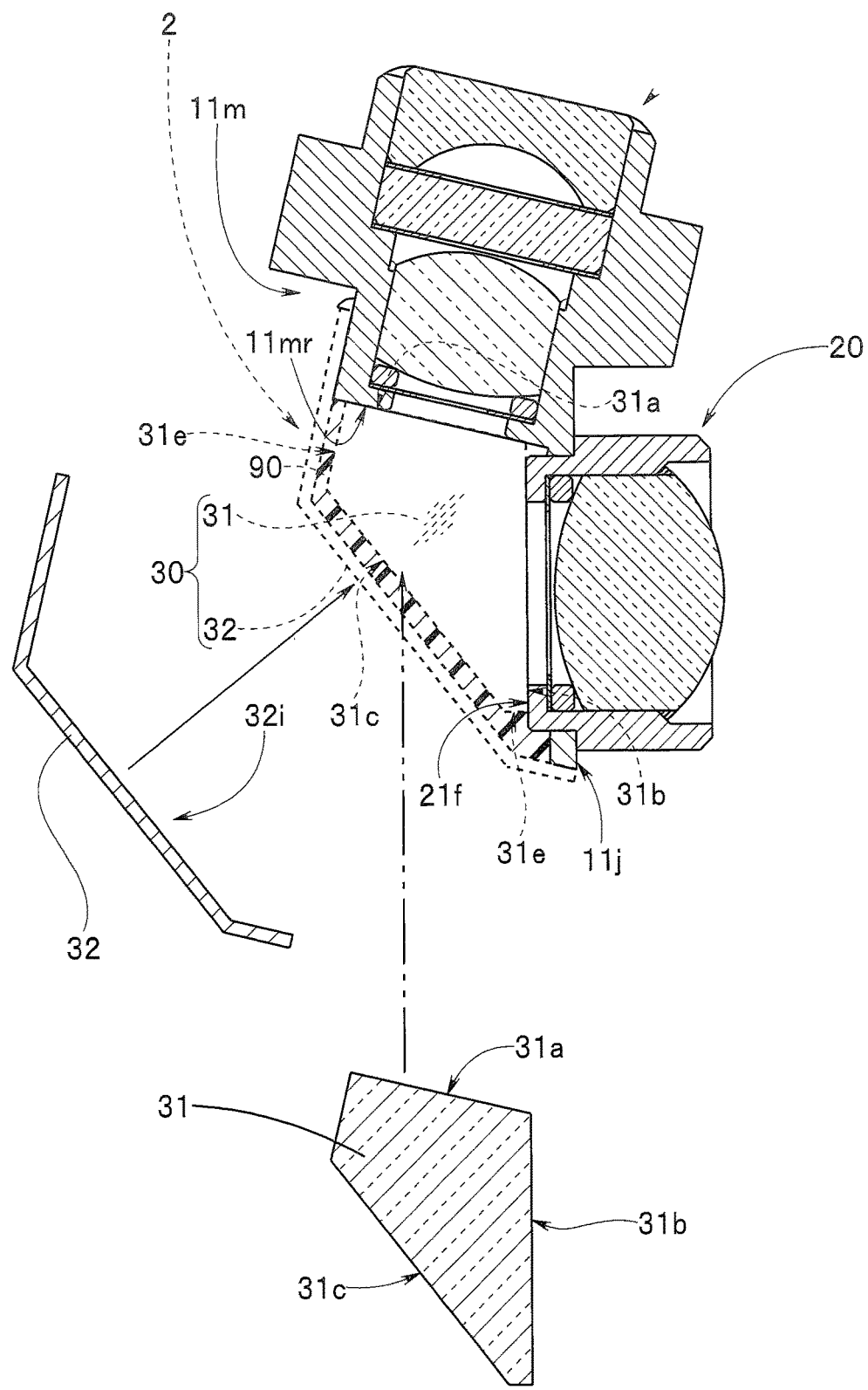
FIG. 5B is a diagram describing the objective lens unit formed by assembling a prism unit to the integrated and assembled first lens unit and second lens unit.

As shown in FIGS. 5A and 5B, the prism 31 is formed in a predetermined shape and includes an incident surface 31a, an emitting surface 31b, and a reflecting surface 31c. Reference sign 30 denotes a housing portion, and reference sign 32 denotes a cover member. The cover member 32 covers entire prism surfaces exposed to the outside, such as the reflecting surface 31c of the prism 31 housed in the prism housing portion 30.

The prism housing portion 30 is provided on a predetermined part of the first lens frame 11, and the prism 31 is housed in the prism housing portion 30. The incident surface 31a of the prism 31 to be housed is brought into contact with and arranged on the main body proximal end surface 11mr of the first lens frame 11 included in the first lens unit 10 and is bonded and fixed. The emitting surface 31b of the prism 31 to be housed is brought into contact with and arranged on the second lens frame distal end surface 21f of the second lens frame 21 included in the second lens unit 20 and is bonded and fixed.

Note that side surfaces 31s of the prism 31 are respectively brought into contact with and arranged on the prism storage side surfaces 11p of the prism housing portion 30 in the housed state.

The reflecting surface 31c and other surfaces 31e that are surfaces other than the incident surface 31a, the emitting surface 31b, and the side surfaces 31s of the prism 31 are exposed from an opening part of the prism housing portion 30. The surface of the prism 31 exposed from the opening part of the prism housing portion 30 is covered by the cover member 32.

The cover member 32 is formed in a predetermined shape. An inner surface 32i of the cover member 32 is divided into a cover region 32ia covering the prism 31 and fixation regions 32ib bonded and fixed in contact with the cover contact surfaces 11c.

The fixation regions 32ib are provided on both side portions of the cover region 32ia. The cover region 32ia covers the reflecting surface 31c and the other surfaces 31e in the state that the fixing regions 32ib are arranged on the cover contact surfaces 11c and bonded and fixed.

As a result, the objective lens unit 2 covered by the prism 31 bonded and fixed to the first lens frame 11 and the second lens frame 21 and covered by the cover member 32 is formed as indicated by dashed lines in FIG. 5B.

Note that when the inner surface 32i of the cover member 32 is a reflecting surface, a light-shielding adhesive 90 is filled in the gap between the inner surface 32i and the surface of the prism 31 to form the objective lens unit 2. On the other hand, when the cover member 32 is light-shielding, the objective lens unit 2 is formed without filling the adhesive 90.

That is, at least one of the cover member 32 and the adhesive 90 is light-shielding.

As shown in FIG. 1, the image pickup device unit 3 includes an image pickup device 41, a circuit substrate 42, a centered lens 43 that also serves as a cover member, an optical lens 44, the image pickup device holding frame 45, a diaphragm 46, a shield member 47, and a heat-shrinkable tube 48.

The image pickup device 41 is a solid-state image pickup device, such as a CCD and a C-MOS, and is mounted on a predetermined position of the circuit substrate 42.

An image pickup surface provided on a front surface of the image pickup device 41 receives light passing through the objective lens unit 2. The image pickup surface is covered by the transparent centered lens 43 and protected. One surface of the centered lens 43 is arranged on the front surface of the image pickup device 41 and integrally bonded and fixed to the image pickup device 41 by a transparent adhesive.

One surface of the optical lens 44 is arranged on a front surface of the centered lens 43 and is integrally bonded and fixed to the optical lens 44 by the transparent adhesive.

The image pickup device holding frame 45 is cylindrical and is a fitting portion for the objective lens unit 2. The image pickup device holding frame 45 includes a space portion 45S and a lens arrangement hole 45h. The lens arrangement hole 45h is a through hole connecting the space portion 45S and the outside, and the optical lens 44 is integrated and fixed to the lens arrangement hole 45h by, for example, an adhesive.

The space portion 45S is a fitting hole for fitting the large diameter portion 21b of the second lens frame 21 of the second lens unit 20. The diaphragm 46 is located in the fitting hole. The diaphragm 46 is arranged on a bottom surface 45b of the space portion 45S and bonded and fixed.

An inner surface of a distal end side end portion of the shield member 47 is arranged on an outer surface of the image pickup device holding frame 45, and the inner surface is integrated and fixed to the holding frame 45 by, for example, a conductive adhesive.

An outer circumference of the shield member 47 is covered by the heat-shrinkable tube 48, and an insulating sealing resin is filled in an internal space 46S of the shield member 47.

Note that various electronic components mounted on the circuit substrate 42, connection terminals (not shown) provided on predetermined positions of the circuit substrate 42, signal lines connected to the connection terminals, and the like are not illustrated.

Assembly of the objective lens unit 2 and the image pickup device unit 3 will be described with reference to FIG. 6.

Figure 6:
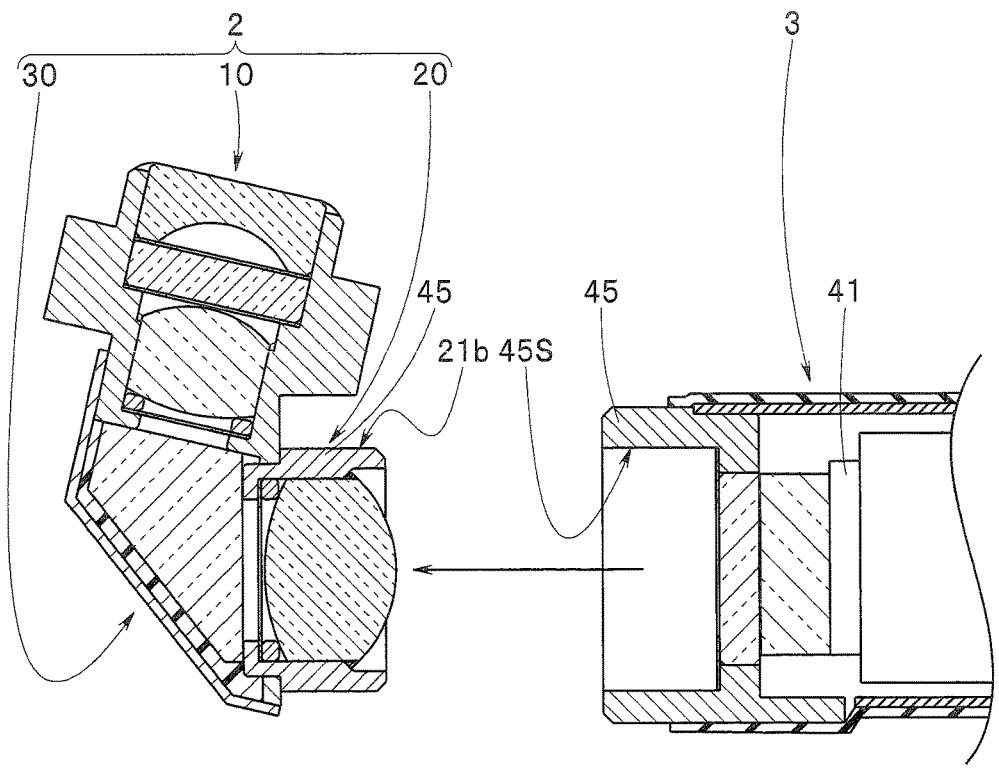
FIG. 6 is a diagram describing assembly of the objective lens unit and an image pickup device unit.

To integrate and assemble the objective lens unit 2 and the image pickup device unit 3 shown in FIG. 6, the second lens frame 21 of the second lens unit 20 included in the objective lens unit 2 and the image pickup device holding frame 45 included in the image pickup device unit 3 are bonded and fixed.

More specifically, the large diameter portion 21b of the second lens frame 21 is fitted and arranged in the space portion 45S of the image pickup device holding frame 45, and the focus is adjusted. A second adhesive is cured in a state that the focus adjustment is completed, and the large diameter portion 21b of the second lens frame 21 is fixed in the space portion 45S of the image pickup device holding frame 45.

As a result, as shown in FIG. 1, the second lens frame 21 of the objective lens unit 2 and the image pickup device holding frame 45 of the image pickup device unit 3 are integrated and fixed by the second frame fixing portion 5 formed by curing of the second adhesive, and the image pickup unit 1 is formed in which the objective lens unit 2 and the image pickup device unit 3 are integrated.

In the present embodiment, a fitting area of a second fitting surface formed by an outer circumference surface of the second lens frame 21 included in the second frame fixing portion 5 and an inner circumference surface of the image pickup device holding frame 45 is set greater than a fitting area of a first fitting surface formed by the inner circumference surface of the lens frame fixing hole 11h5 included in the first frame fixing portion 4 and an outer circumference surface of the second lens frame 21.

Note that the second adhesive is an adhesive with a glass transition temperature lower than the first adhesive. For example, the first adhesive is an epoxy resin material, and the second adhesive is a silicone resin material. When adhesives with the same resin material are used, the first adhesive and the second adhesive have adjusted glass transition temperatures.

The second adhesive is applied in advance to an outer circumference surface of the large diameter portion 21b before the large diameter portion 21b that is a second fitting surface is fitted and arranged in the space portion 45S of the image pickup device holding frame 45 that is a second fitting surface, or the second adhesive is supplied to a gap between the outer circumference surface of the large diameter portion 21b and the inner circumference surface of the space portion 45S after the large diameter portion 21*b* is fitted and arranged in the space portion 45S.

In the image pickup unit 1 completed with the assembly, whether there is waste, such as an adhesive residue, is inspected.

An image pickup unit that has failed the inspection in the present embodiment (described as an image pickup unit N) is not discarded, and the image pickup unit is disassembled into the objective lens unit 2 and the image pickup device unit 3.

A worker performs work for disassembling the image pickup unit N into the objective lens unit 2 and the image pickup device unit 3 while heating the image pickup device holding frame 45 and the second lens frame 21 of the image pickup unit N by a heater or a burner.

Note that if there is a predetermined difference between the glass transition temperatures of the resin materials, an apparatus, such as a spot heater, is used for the heating. On the other hand, if the difference between the glass transition temperatures of the resin materials is small, such as a temperature difference of 10° C., a furnace, such as a drying furnace, is used to heat the resin materials up to predetermined temperatures. In this way, stable disassemble work can be performed.

As the temperatures of the image pickup device holding frame 45 and the second lens frame 21 rise due to the heating, the temperatures of the second frame fixing portion 5 and the first frame fixing portion 4 also rise. In the image pickup unit 1 of the present embodiment, the first frame fixing portion 4 and the second frame fixing portion 5 are formed by the first adhesive and the second adhesive with different glass transition temperatures. The glass transition temperature of the second adhesive is set lower than the glass transition temperature of the first adhesive.

Therefore, the second adhesive of the second frame fixing portion 5 starts to soften at a predetermined temperature lower than the first adhesive of the first frame fixing portion 4.

In this case, since the worker applies predetermined force to the objective lens unit 2 and the image pickup device unit 3, the second frame fixing portion 5 with a large fitting area in the image pickup unit N is broken up, and the image pickup unit N is disassembled into the objective lens unit 2 and the image pickup device unit 3.

As a result, the objective lens unit 2 and the image pickup device unit 3 of the image pickup unit N can be reused through predetermined work.

Note that when an epoxy resin material with a glass transition temperature sufficiently higher than a normal temperature environment is adopted as the first adhesive, and a silicone resin material is adopted as the second adhesive, the disassemble work can be performed under the normal temperature environment for performing the disassemble work without the heating, because the glass transition temperature of the silicone adhesive is generally below zero.

Figure 7A:
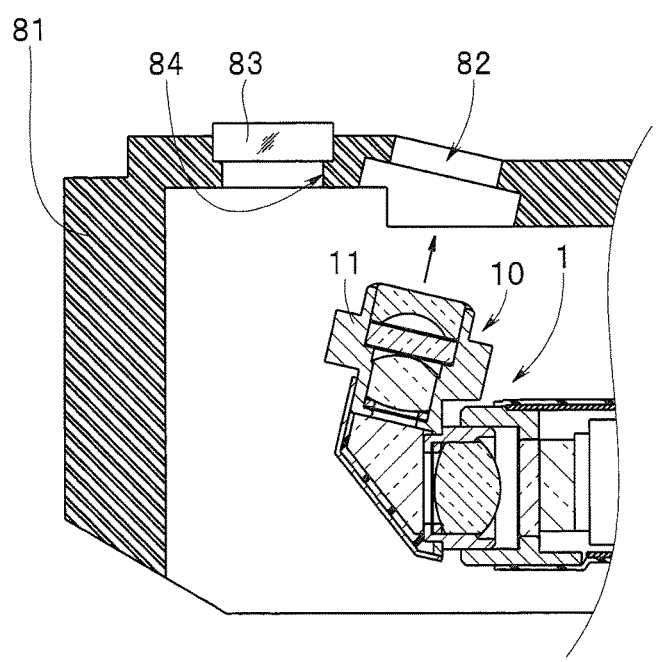
FIG. 7A is a diagram showing the image pickup device unit arranged on a distal end rigid member.
Figure 7B:
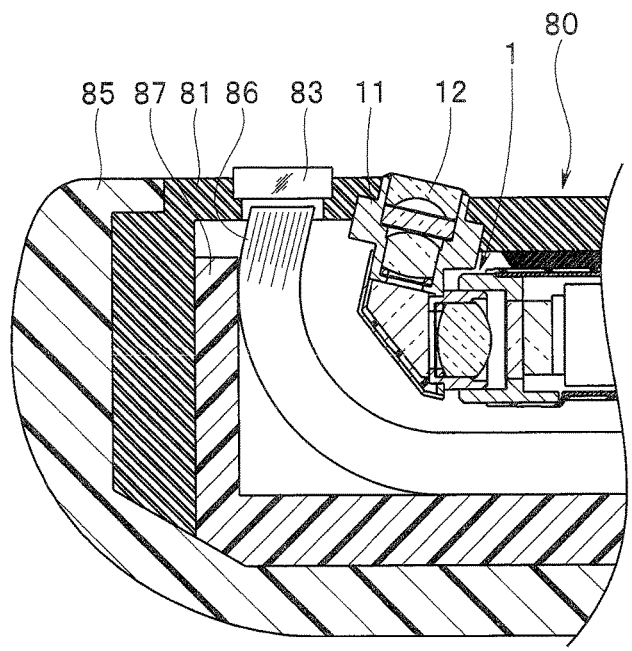
FIG. 7B is a diagram showing a side-view type endoscope including the image pickup device unit.

Note that the image pickup unit 1 that has passed the inspection is attached to a distal end rigid member 81 as shown in FIG. 7A, and a side-view type endoscope 80 is formed as shown in FIG. 7B.

Reference sign 82 of FIG. 7A denotes an image pickup unit opening, and the first lens frame 11 of the image pickup unit 1 is attached to the image pickup unit opening 82 provided on the distal end rigid member 81. Reference sign 83 denotes an illumination lens which is fixed and installed on an illumination opening 84.

Reference sign 85 of FIG. 7B denotes a distal end cover, and the distal end rigid member 81 is integrally fixed and installed in the distal end cover 85. Reference sign 86 denotes a light guide bundle, and a distal end surface of the light guide bundle 86 is faced by the illumination lens 83. Reference sign 87 denotes a bundle holding member, and the bundle holding member 87 is a resin member configured to hold the light guide bundle 86. Note that the holding member 87 is not limited to the resin member, and the holding member 87 may be a metal member.

In the side-view type endoscope 80, so-called lens breakage, such as cracking and fracture, may occur in the first optical lens 12 during the use, or lens fogging may occur. This may obstruct the observation.

The side-view type endoscope 80 with the lens breakage or lens fogging is sent for repair. The image pickup unit 1 is used for the side-view type endoscope 80. Therefore, the image pickup unit 1 can be disassembled into the objective lens unit 2 and the image pickup device unit 3 as described above. The objective lens unit 2 can be discarded, and on the other hand, the image pickup device unit 3 can be reused.

In this way, the glass transition temperature of the second adhesive forming the second frame fixing portion 5 configured to bond and fix the objective lens unit 2 and the image pickup device unit 3 is set lower than the glass transition temperature of the first adhesive forming the first frame fixing portion 4 configured to bond and fix the lens units 10 and 20 included in the objective lens unit 2. As a result, the second frame fixing portion 5 with a large fitting area can be broken up without breaking up the first frame fixing portion 4 with a small fitting area, and the image pickup unit 1 can be easily disassembled into the objective lens unit 2 and the image pickup device unit 3.

Figure 8:
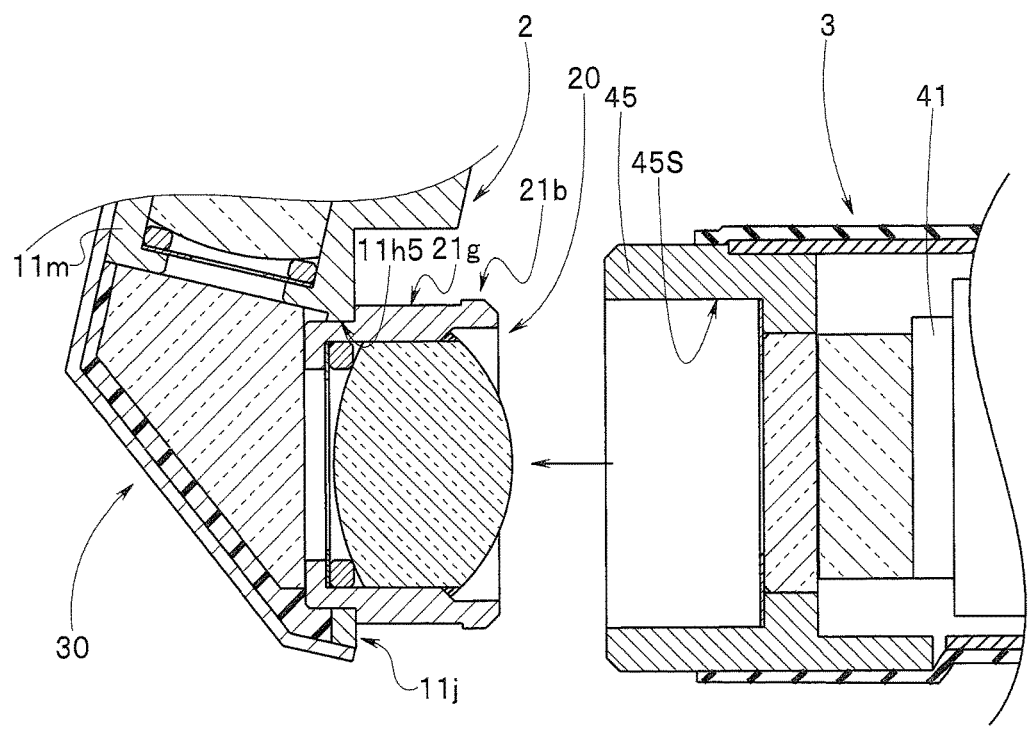
FIG. 8 is a diagram describing another configuration of a second lens frame included in the second lens unit.

Note that as shown in FIG. 8, a circumferential groove 21*g* is provided on the large diameter portion 21*b* of the second lens frame 21 fitted and arranged in the space portion 45S of the image pickup device holding frame 45. The circumferential groove 21*g* is provided such that a surface area of the large diameter portion 21*b* is smaller than an inner surface area of the lens frame fixing hole 11*h*5 provided on the coupling portion 11*j*.

According to the configuration, a bonding area of the second frame fixing portion 5 formed by the second adhesive is smaller than a bonding area of the first frame fixing portion 4 formed by the first adhesive.

As a result, when the worker heats the image pickup device holding frame 45 and the second lens frame 21 to disassemble the image pickup unit N, the worker can break up the second frame fixing portion 5 of the image pickup unit N by reducing the heating time upon the start of the softening of the second adhesive forming the second frame fixing portion 5, and the worker can more smoothly disassemble the image pickup unit N into the objective lens unit 2 and the image pickup device unit 3.

The bonding area of the second frame fixing portion 5 formed by the second adhesive with a glass transition temperature lower than the first adhesive is set smaller than the bonding area of the first frame fixing portion 4 formed by the first adhesive. Therefore, a predetermined amount of force can be applied to perform the disassemble work without heating the image pickup device holding frame 45 and the second lens frame 21 of the image pickup unit N, and the second frame fixing portion 5 can be broken up to easily disassemble the image pickup unit 1 into the objective lens unit 2 and the image pickup device unit 3.

Figure 9A:
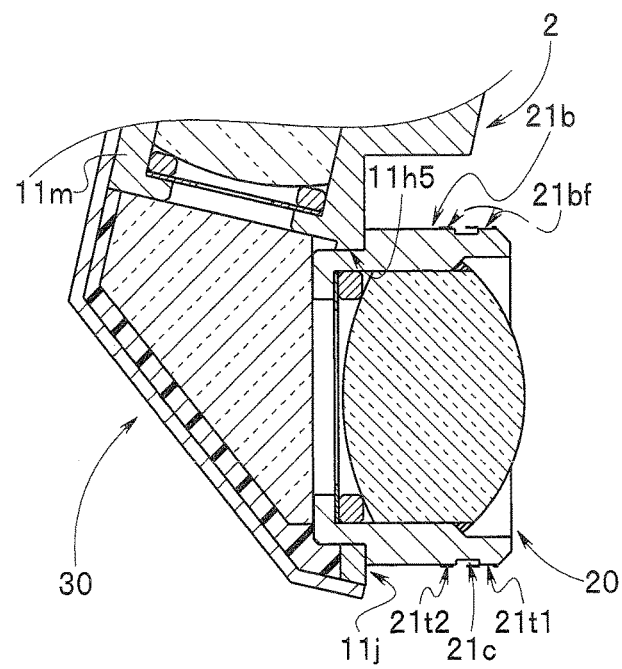
FIG. 9A is a diagram showing another configuration of the second lens frame included in the second lens unit and a state of assembly to an image pickup device holding frame.

As shown in FIG. 9A, a bonding surface portion and a non-bonding surface portion may be provided on a fitting surface 21*bf* of the large diameter portion 21*b* of the second lens frame 21 fitted and arranged in the space portion 45S of the image pickup device holding frame 45.

A circumferential direction concave portion 21*c* is provided, and the fitting surface 21*bf* of the large diameter portion 21*b* is divided into the circumferential direction concave portion 21*c* serving as a bonding surface portion, a first fitting surface portion 21*t*1, and a second fitting surface portion 21*t*2. The circumferential direction concave portion 21*c* is an adhesive reservoir and is provided between the first fitting surface portion 21*t*1 and the second fitting surface portion 21*t*2.

Figure 9B:
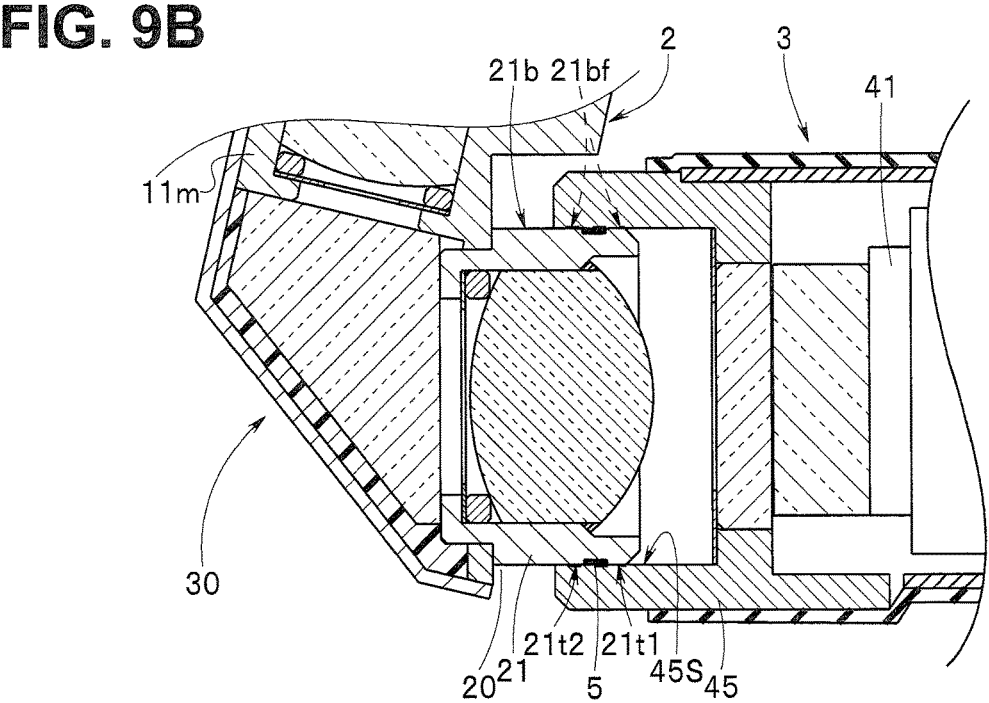
FIG. 9B is a diagram showing another configuration of the second lens frame included in the second lens unit and a state of assembly to the image pickup device holding frame.

As shown in FIG. 9B, the fitting surface 21*bf* of the large diameter portion 21*b* is fitted and arranged in the space portion 45S of the image pickup device holding frame 45. In this case, the first fitting surface portion 21*t*1 of the large diameter portion 21*b* is brought into contact with and arranged in the space portion 45S of the image pickup device holding frame 45 through predetermined fitting.

In the present embodiment, a width of the circumferential direction concave portion 21*c* is set such that the bonding area of the second frame fixing portion 5 is smaller than the bonding area of the first frame fixing portion 4.

According to the configuration, an outer circumference surface of the first fitting surface portion 21*t*1 that is the non-bonding surface portion of the large diameter portion 21*b* is arranged on the inner circumference surface of the space portion 45S of the image pickup device holding frame 45 without the adhesive, and highly accurate assembly can be realized.

This can prevent the adhesive applied to the circumferential direction concave portion 21*c* from entering a gap between the first fitting surface portion 21*t*1 and the inner circumference surface of the space portion 45S in the fitting arrangement work and can prevent the adhesive from becoming waste after passing through the gap and exceeding the proximal end surface of the second lens frame 21.

As a result, defective inspections in which the adhesive residue becomes waste are reduced.

Figure 9C:
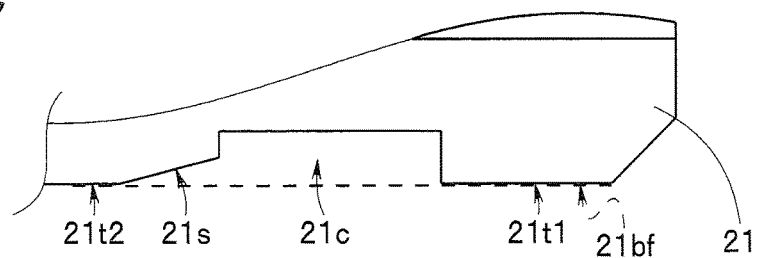
FIG. 9C is a diagram showing another configuration of the second lens frame included in the second lens unit and a state of assembly to the image pickup device holding frame.

As shown in FIG. 9C, an inclined surface 21*s* extending toward the second fitting surface portion 21*t*2 side can be provided to more effectively prevent the adhesive applied in the circumferential direction concave portion 21*c* from passing through the first fitting surface portion 21*t*1 and entering the proximal end surface side of the second lens frame 21 to become waste in the fitting arrangement work.

Figure 10:
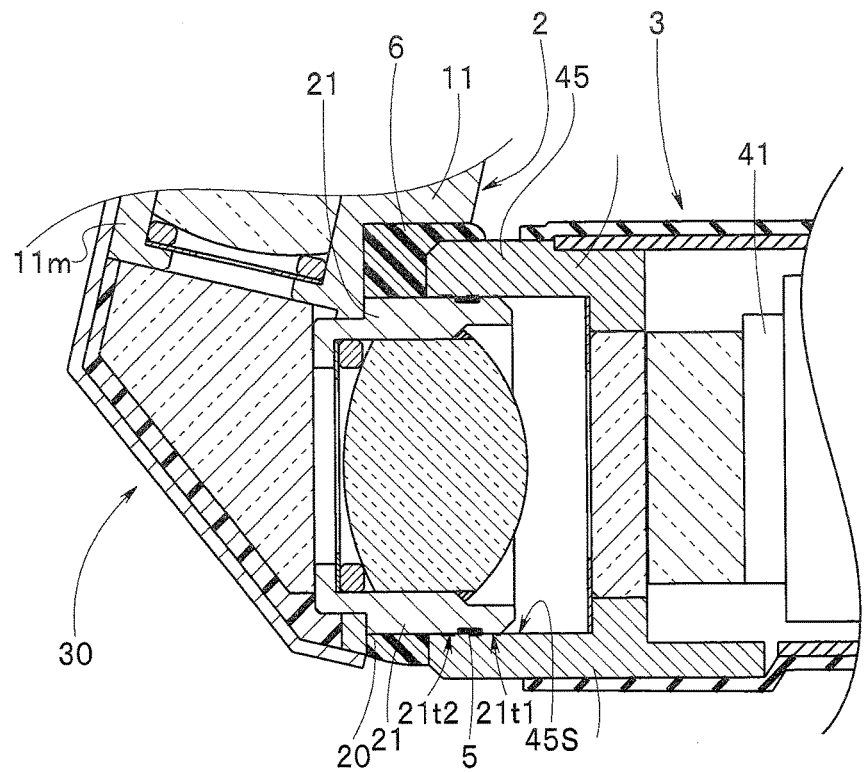
FIG. 10 is a diagram describing an example of configuration for improving a fixation strength of the objective lens unit and the image pickup device unit.

Note that in the image pickup unit 1 that has passed the inspection by forming the image pickup unit 1 as shown in FIG. 9B, a third fixing portion 6 is provided in addition to the second frame fixing portion 5 as shown in FIG. 10. The third fixing portion 6 is formed by applying the second adhesive in close contact with the first lens frame 11, the second lens frame 21, and the image pickup device holding frame 45.

According to the configuration, the third fixing portion 6 is provided in addition to the second frame fixing portion 5, and this can realize the image pickup unit 1 in which fixing strength of the objective lens unit 2 and the image pickup device unit 3 is improved.

When, for example, lens breakage occurs in the image pickup unit 1 provided with the third fixing portion 6, the third fixing portion 6 is broken up first, and then the image pickup unit 1 is disassembled into the objective lens unit 2 and the image pickup device unit 3 as described above. The image pickup device unit 3 is reused.

Figure 11:
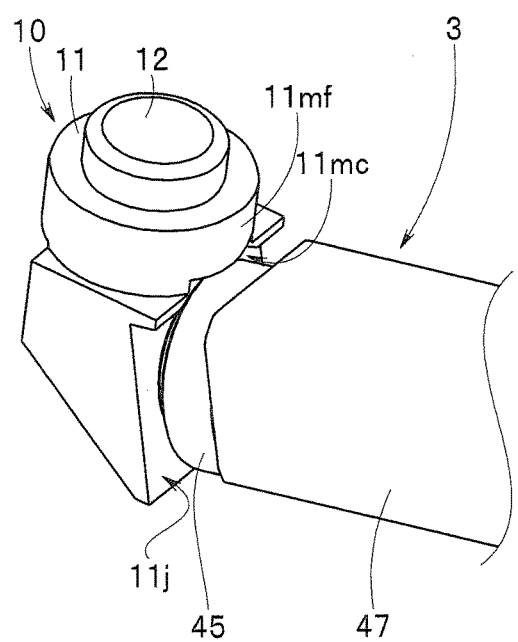
FIG. 11 is a diagram describing another example of configuration for improving the fixation strength of the objective lens unit and the image pickup device unit.

As shown in FIG. 11, a notch portion 11*mc* is provided on a predetermined part of the flange portion 11*mf* of the frame main body 11*m* included in the first lens frame 11. To arrange part of the device holding frame 45 in the notch portion 11*mc*, an outside diameter of the holding frame 45 is extended with respect to an axis center of the frame 45 to enlarge the diameter.

In this way, a thickness of the annular image pickup device holding frame 45 can be increased while maintaining an inside diameter, and the area of the distal end surface of the image pickup device holding frame 45 can be increased. The increased distal end surface of the image pickup device holding frame 45 is set as a bonding surface of the coupling portion 11*j* and the coupling portion proximal end surface 11*jr* of the first lens frame 11.

According to the configuration, the second frame fixing portion 5 is provided to bond and fix the increased distal end surface of the image pickup device holding frame 45 to the coupling portion 11*j* of the first lens frame 11, and this can realize the image pickup unit 1 in which the fixation strength of the objective lens unit 2 and the image pickup device unit 3 is improved.

Figure 12:
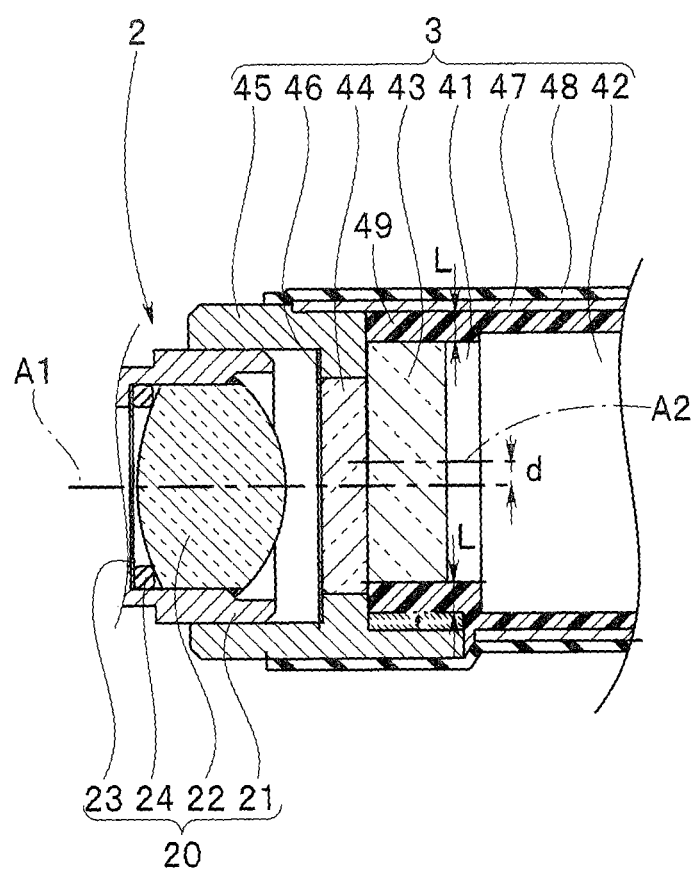
FIG. 12 is a diagram describing a configuration of protecting an image pickup device from residual stress in a configuration in which an optical axis and a center line of the image pickup device are displaced.

As shown in FIG. 12, when an optical axis A1 and a center line A2 of the image pickup device 41 are displaced (d), a space of the image pickup device 41 in a side surface direction becomes non-uniform. Residual stress at cure shrinkage of the sealing resin filled in the non-uniform space is applied in one direction, and the image pickup device 41 may be broken up.

To eliminate the malfunction, when the space of the image pickup device 41 in the side surface direction is non-uniform, a device frame arrangement space 45S1 is displaced from a position of a solid line to a position of an alternate long and two short dashes line such that an inner circumference surface 45*f* of the device frame arrangement space 45S1 of the image pickup device holding frame 45 and a side surface of the image pickup device 41 become uniform.

As a result, a distance L between the inner circumference surface 45*f* of the device frame arrangement space 45S1 and the side surface of the image pickup device 41 becomes uniform, and the residual stress at the cure shrinkage of the sealing resin 49 filled in the uniform space becomes uniform. The breakage of the image pickup device 41 due to the residual stress can be prevented.

Here, the large diameter portion 21*b* is fitted and arranged in the space portion 45S of the image pickup device holding frame 45 in the embodiment described above. However, the image pickup device holding frame 45 may be fitted and arranged in an inner hole of the large diameter portion 21*b*.

Figure 13:
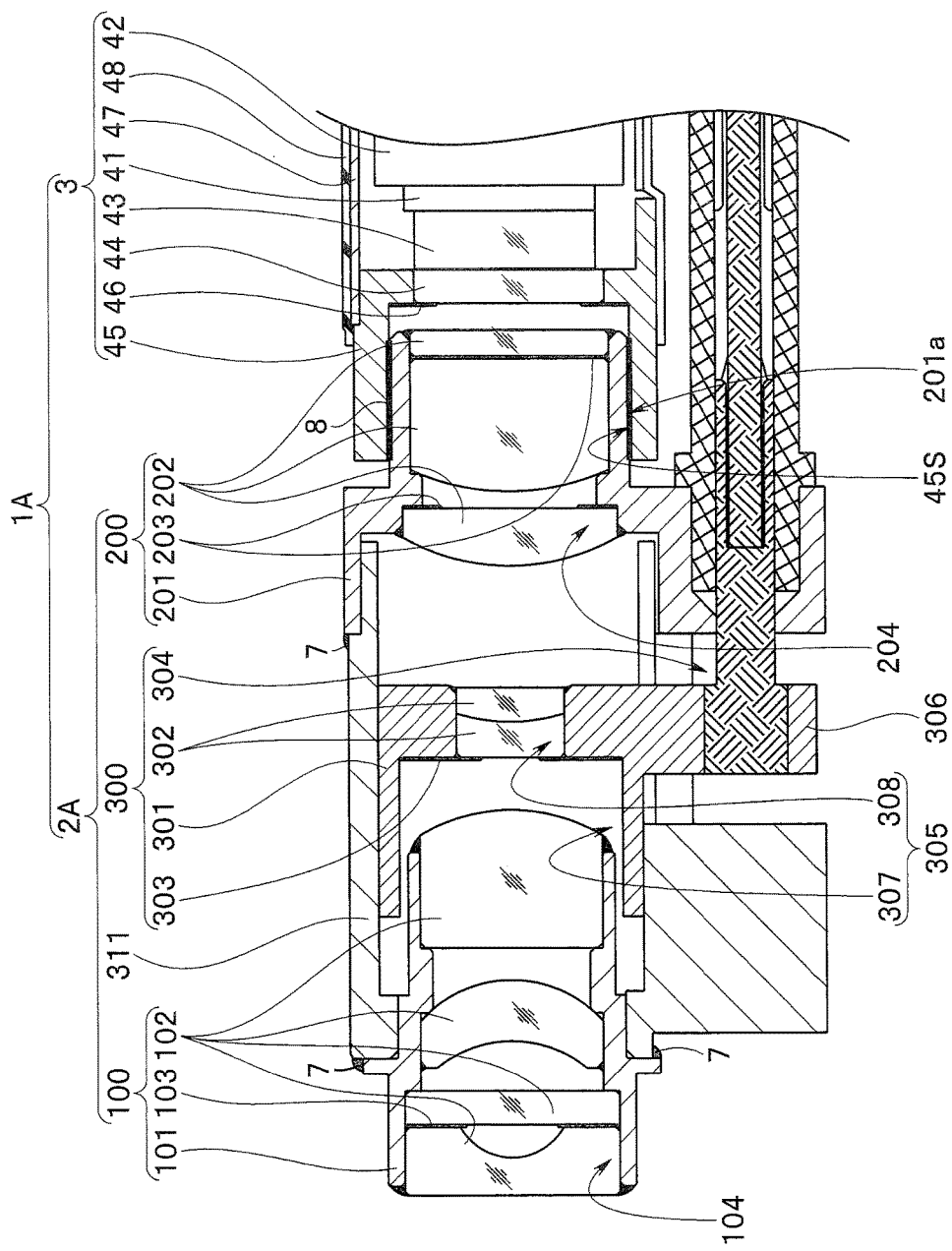
FIG. 13 is a diagram describing another example of configuration of the image pickup unit for endoscope.

The image pickup unit 1 is for the side-view type endoscope in the embodiment described above. However, the image pickup unit is not limited to the image pickup unit for the side-view type endoscope, and the image pickup unit may be an image pickup unit for a front-view type endoscope as shown in FIG. 13.

Note that, for components of the image pickup unit for front-view type endoscope, the same reference signs are provided to the same members as in the image pickup unit 1, and the description will not be repeated.

The image pickup unit 1A for front-view type endoscope includes an objective lens unit 2A and the image pickup device unit 3. The objective lens unit 2A includes a first lens unit 100, a second lens unit 200, a moving lens unit 300, and a coupling frame 311.

Reference sign 7 denotes first frame fixing portions which are fixed by metal junction, such as soldering and brazing. On the other hand, reference sign 8 denotes a second frame fixing portion which is bonded and fixed by an adhesive.

The first lens unit 100 includes a first lens frame 101, a plurality of optical lenses 102 that are a plurality of optical members, and a diaphragm 103. Note that the number of diaphragms is not limited to one, and more diaphragms may be included. An interval ring may also be provided.

The first lens frame 101 has a predetermined pipe shape and includes a first frame hole 104. The first frame hole 104 is a stepped through hole in a predetermined shape, and an optical member is appropriately fixed and installed.

The second lens unit 200 includes a second lens frame 201, a plurality of optical lenses 202 that are a plurality of optical members, and a plurality of diaphragms 203. Note that an interval ring may also be provided.

The second lens frame 201 has a predetermined pipe shape and includes a second frame hole 204. The second frame hole 204 is a stepped through hole in a predetermined shape, and an optical member is appropriately fixed and installed.

The moving lens unit 300 includes a moving lens frame 301, a plurality of optical lenses 302, a diaphragm 303, and a moving lens frame movement mechanism 304.

Note that the moving lens frame movement mechanism 304 is a publicly-known technique and will not be described. The number of diaphragms is not limited to one, and more diaphragms may be included. An interval ring may also be provided.

The moving lens frame 301 includes a frame main body 305 and a movement rod 306. The frame main body 305 is cylindrical and includes a concave portion 307 and a third frame hole 308. The first lens frame 101 is loosely fitted and arranged in the concave portion 307.

The third frame hole 308 is an axial direction through hole connecting the concave portion 307 and the outside, and the optical lenses 302 are fixed and installed. The diaphragm 303 is fixed and installed on a bottom surface of the concave portion 307, for example. A distal end portion of the moving lens frame movement mechanism 304 is integrated and fixed to the movement rod 306.

The coupling frame 311 has a predetermined pipe shape and includes a fourth frame hole 312 that is an axial direction through hole and a long hole 313 connecting the fourth frame hole 312 and the outside. The long hole 313 is provided on a predetermined position of a side portion of the coupling frame 311, and the movement rod 306 is arranged in a manner that the movement rod 306 can freely move back and forth.

The first lens frame 101 is fitted and arranged on a distal end opening side of the fourth frame hole 312, and the first frame fixing portions 7 based on metal junction, such as soldering, are provided for integrated fixation. On the other hand, the second lens frame 201 is fitted and arranged on a proximal end opening side of the fourth frame hole 312, and the first frame fixing portions 7 are provided for integrated fixation.

The frame main body 305 of the moving lens frame 301 is arranged in the fourth frame hole 312 in a manner that the frame main body 305 can freely move back and forth.

As a result, the objective lens unit 2A is formed in which the first lens unit 100, the second lens unit 200, and the coupling frame 311 are integrated and fixed, and the moving lens unit 300 is arranged in the coupling frame 311 in a manner that the moving lens unit 300 can freely move back and forth.

To integrate and assemble the objective lens unit 2A and the image pickup device unit 3 as illustrated in the drawing, the second lens frame 201 of the second lens unit 200 included in the objective lens unit 2A and the image pickup device holding frame 45 included in the image pickup device unit 3 are bonded and fixed.

More specifically, a small diameter portion 201a of the second lens frame 201 is fitted and arranged in the space portion 45S of the image pickup device holding frame 45, and the focus is adjusted. The adhesive is cured in a state that the focus adjustment is completed, and the small diameter portion 201a of the second lens frame 201 is fixed in the space portion 45S of the image pickup device holding frame 45.

As a result, the second lens frame 201 of the objective lens unit 2A and the image pickup device holding frame 45 of the image pickup device unit 3 are integrated and fixed by the second frame fixing portion 8 formed by curing of the adhesive as illustrated in the drawing, and the image pickup unit 1A is formed in which the objective lens unit 2A and the image pickup device unit 3 are integrated.

Note that the adhesive is a silicone resin material or an epoxy resin material with the melting point lower than the soldering. The adhesive is applied in advance to an outer circumference surface of the small diameter portion 201a before the small diameter portion 201a is fitted and arranged in the space portion 45S, or the adhesive is supplied to a gap between the outer circumference surface of the small diameter portion 201a and an inner circumference surface of the space portion 45S after the small diameter portion 201a is fitted and arranged in the space portion 45S.

In the image pickup unit 1A completed with the assembly, whether there is waste, such as an adhesive residue, is inspected.

An image pickup unit that has failed the inspection in the present embodiment (described as an image pickup unit NA) is not discarded, and the image pickup unit NA is disassembled into the objective lens unit 2A and the image pickup device unit 3.

More specifically, the worker performs work of disassembling the image pickup unit NA into the objective lens unit 2A and the image pickup device unit 3 while heating the image pickup device holding frame 45 and the second lens frame 201 of the image pickup unit NA by a heater or a burner.

As the temperatures of the image pickup device holding frame 45 and the second lens frame 21 rise due to the heating, the temperatures of the metal-junction first frame fixing portions 7 and the bonded and fixed second frame fixing portion 8 also rise. In the image pickup unit 1A of the present embodiment, the first frame fixing portions 7 and the second frame fixing portion 8 have different melting points. Therefore, the adhesive of the second frame fixing portion 8 starts to soften at a predetermined temperature lower than the soldering of the first frame fixing portions 7.

In this case, since the worker applies predetermined force to the objective lens unit 2A and the image pickup device unit 3, the second frame fixing portion 8 of the image pickup unit NA is broken up, and the image pickup unit NA is disassembled into the objective lens unit 2A and the image pickup device unit 3.

As a result, the objective lens unit 2A and the image pickup device unit 3 of the image pickup unit NA can be reused through predetermined work.

Note that the image pickup unit 1A that has passed the inspection is attached to a distal end rigid member not shown, and a front-view type endoscope (not shown) is formed.

In this way, the objective lens unit 2A and the image pickup device unit 3 are fixed by the second frame fixing portion 8 based on bonding and fixation, and the plurality of lens units 100 and 200 and the coupling frame 311 included in the objective lens unit 2A are fixed by the first frame fixing portions 7 based on metal junction. As a result, the first frame fixing portions 7 are not melted, and the second frame fixing portion 8 based on the adhesive can be broken up to easily disassemble the image pickup unit 1A into the objective lens unit 2A and the image pickup device unit 3.

In the present embodiment, the first frame fixing portions 7 of the image pickup unit 1A for the front-view type endoscope are based on the metal junction. However, the first frame fixing portions 7 may be the first frame fixing portion 4 formed by the first adhesive, and the second frame fixing portion 8 may be the second frame fixing portion 5 formed by the second adhesive as in the image pickup unit 1.

The image pickup unit 1A is not limited to an image pickup unit including the moving lens unit 300, and a configuration that does not require the moving lens unit 300 is also possible.

The first frame fixing portion 4 based on the first adhesive in the image pickup unit 1 may be the first frame fixing portions 7 based on the metal junction.

Note that the present invention is not limited only to the embodiment described above, and various modifications can be carried out without departing from the scope of the invention.

The present invention can realize an image pickup unit for endoscope that can disassemble and reuse a lens unit and an image pickup device unit after breaking up a predetermined frame fixing portion without breaking the lens unit and the image pickup device unit, while reducing the diameter of an insertion portion and shortening a rigid portion.

What is claimed is:
1. An image pickup unit for endoscope comprising:
an objective lens unit including a first lens frame and a second lens frame;
an image pickup device unit including an image pickup device and a holding frame configured to hold the image pickup device;
a first frame fixing portion at which the first lens frame and the second lens frame are fitted to each other; and
a second frame fixing portion at which the second lens frame and the holding frame are fitted to each other,
wherein the first lens frame and the second lens frame are fitted to each other with a first fitting area and bonded and fixed to each other with a first adhesive at the first frame fixing portion,
the second lens frame and the holding frame are fitted to each other with a second fitting area and bonded and fixed to each other with a second adhesive at the second frame fixing portion,
the second fitting area is larger than the first fitting area, and
the second adhesive has a glass transition temperature lower than a glass transition temperature of the first adhesive.

2. The image pickup unit for endoscope according to claim 1, wherein
an outer circumference surface of the second lens frame forming a fitting portion of the second lens frame and the holding frame is provided with:
a bonding surface portion configured to integrate and fix the second lens frame and the holding frame by the second adhesive; and
a non-bonding surface portion where the second lens frame and the holding frame come into direct contact with each other.

3. The image pickup unit for endoscope according to claim 2, wherein
a bonding surface portion formed by a concave portion is provided on a middle portion of an outer circumference surface of the second lens frame forming the fitting portion.

4. An image pickup unit for endoscope comprising:
an objective lens unit including a first lens frame and a second lens frame;
an image pickup device unit including an image pickup device and a holding frame configured to hold the image pickup device;
a first frame fixing portion at which the first lens frame and the second lens frame are fitted to each other; and
a second frame fixing portion at which the second lens frame and the holding frame are fitted to each other,
wherein the first lens frame and the second lens frame are fitted to each other with a first fitting area and joined to each other by a metal junction with a metal junction member at the first frame fixing portion,
the second lens frame and the holding frame are fitted to each other with a second fitting area and bonded and fixed to each other with an adhesive at the second frame fixing portion,
the second fitting area is larger than the first fitting area, and
the adhesive has a melting point lower than a melting point of the metal junction member.

* * * * *